US00PP34442P2

(12) United States Plant Patent
Ranney et al.

(10) Patent No.: US PP34,442 P2
(45) Date of Patent: Jul. 26, 2022

(54) ***MAHONIA* PLANT NAMED 'NCMH1'**

(50) Latin Name: *Mahonia*
Varietal Denomination: 'NCMH1'

(71) Applicant: North Carolina State University, Raleigh, NC (US)

(72) Inventors: Thomas Ranney, Arden, NC (US); Darren H. Touchell, Arden, NC (US); Andra Windorf Nus, Mills River, NC (US); Irene Palmer, Mills River, NC (US); Nathan Lynch, Mills River, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/501,727

(22) Filed: Oct. 14, 2021

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Myers Bigel, P.A.

(57) ABSTRACT

'NCMH1' is a new cultivar of *Mahonia* with a compact habit, dark green semi-evergreen foliage, and showy yellow flowers.

3 Drawing Sheets

Latin name of the genus and species: The Latin name of the novel, ornamental plant variety disclosed herein is *Mahonia*.

Variety denomination: The inventive cultivar of *Mahonia* disclosed herein has been given the varietal denomination 'NCMH1'.

BACKGROUND OF THE INVENTION

The present invention comprises a new and distinct *Mahonia* cultivar hereinafter referred to by the cultivar name 'NCMH1'. This new *Mahonia* was developed through a breeding program in Mills River, N.C. 'NCMH1' was selected from a population of seedlings grown from a controlled cross of *Mahonia* x *media* 'Winter Sun' (unpatented) x *Mahonia* 'Soft Caress' (U.S. Plant Pat. No. 20,183). The first asexual propagation of 'NCMH1' was carried out in December 2014 by rooting stem cuttings in Mills River, N.C. and has been asexually reproduced repeatedly by vegetative cuttings over a four-year period. 'NCMH1' roots from hardwood cuttings were treated with a basal dip of 5,000-10,000 ppm indole butyric acid (potassium salt) in water. 'NCMH1' has been found to retain its distinctive characteristics through successive asexual propagations.

SUMMARY OF THE INVENTION

'NCMH1' is distinguishable from other *Mahonia* cultivars, when grown under standard horticultural practices in Mills River, N.C., by its compact habit with dense branching; soft, dark evergreen foliage with a refined look; and long racemes of showy yellow flowers produced sporadically in fall, winter, and spring.

BRIEF DESCRIPTION OF THE DRAWINGS

This new *Mahonia* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Mahonia*.

DETAILED BOTANICAL DESCRIPTION

Figure 1:
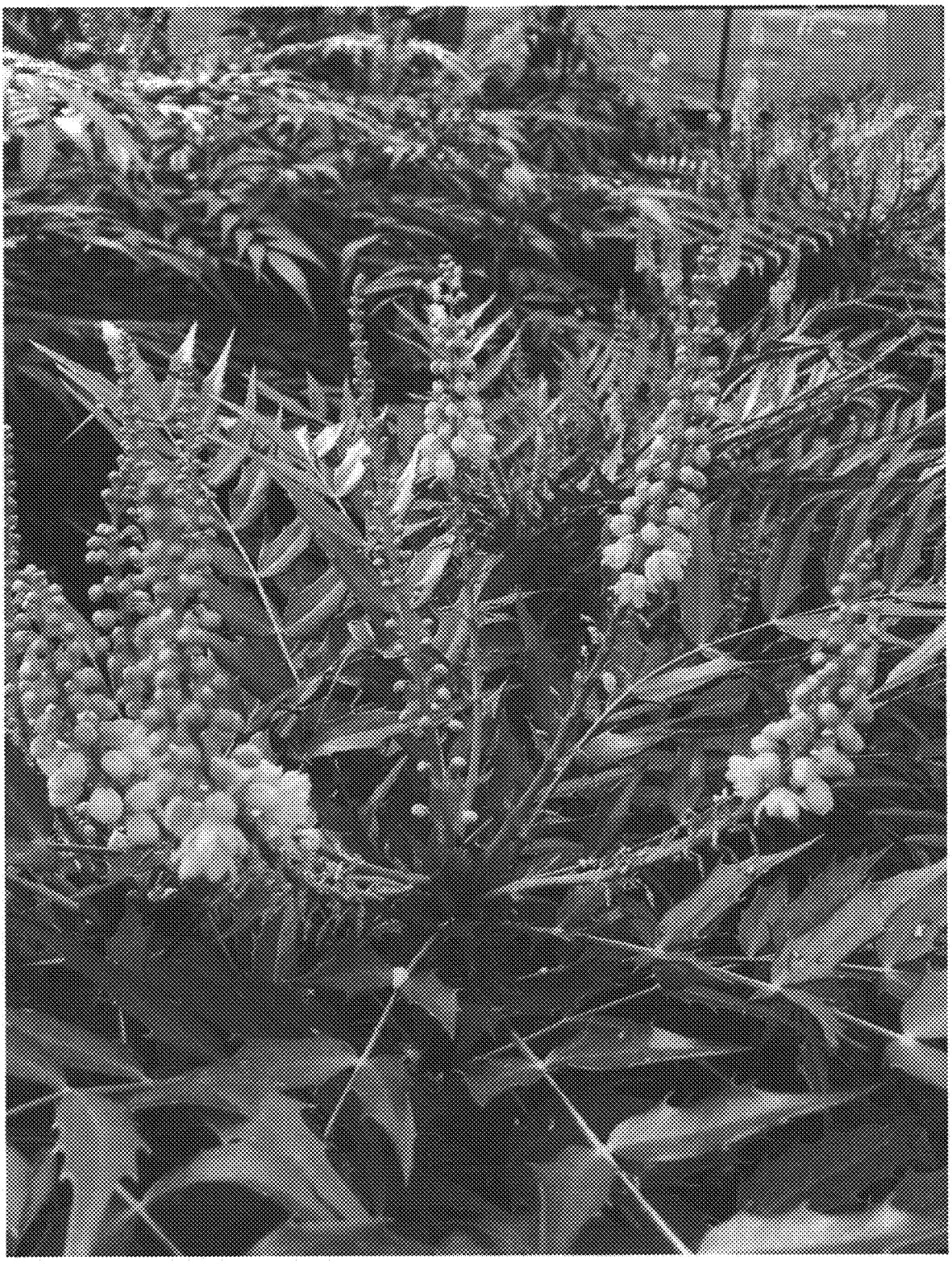
FIG. 1 is a color photograph of a typical 3-year-old specimen of *Mahonia* 'NCMH1' grown under standard horticultural practices showing yellow (RHS 7A) inflorescences and long racemes.
Figure 2:
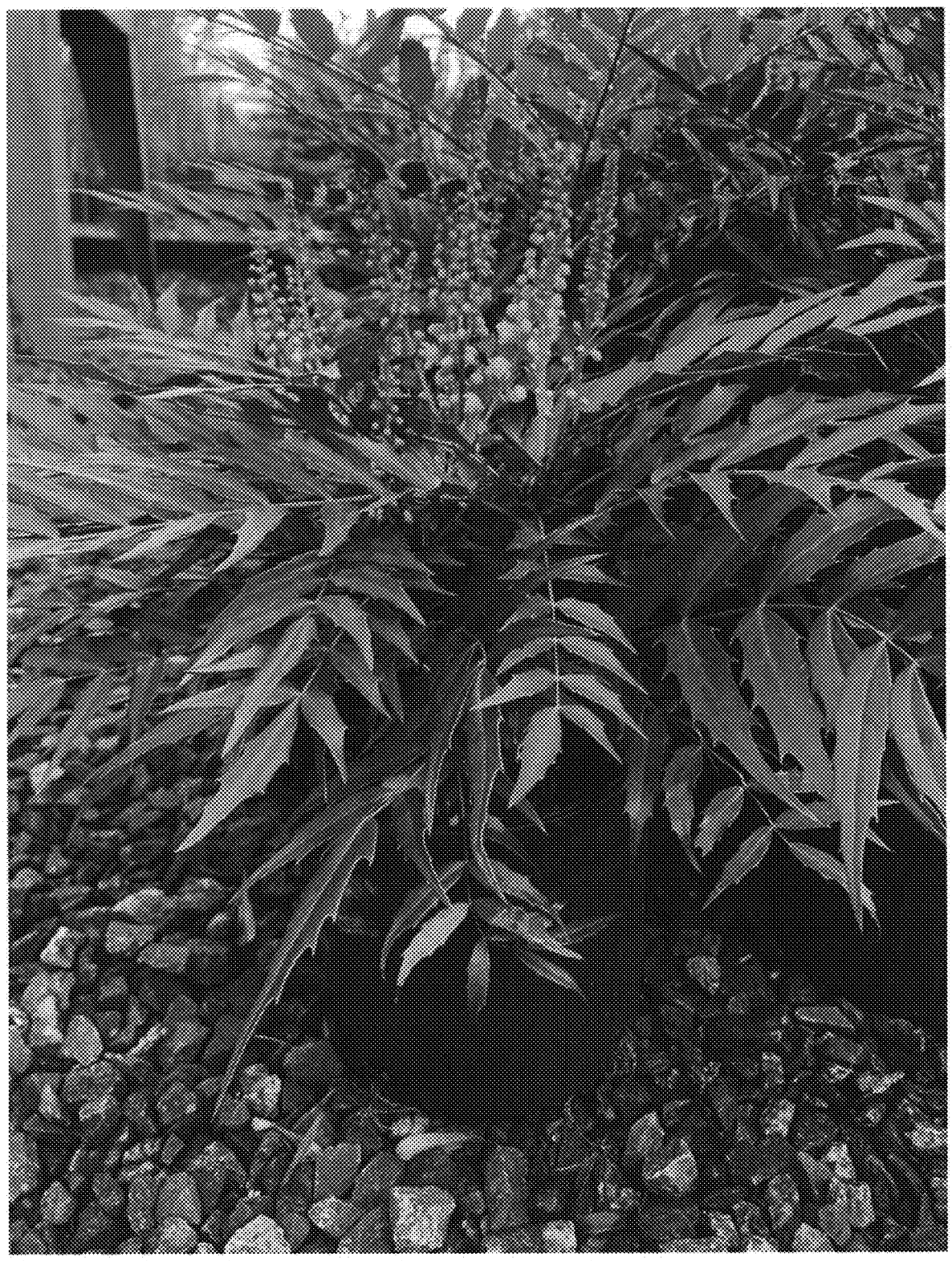
FIG. 2 is a color photograph of a typical 3-year-old specimen of *Mahonia* 'NCMH1' grown under standard horticultural practices showing the habit of a container-grown plant.
Figure 3:
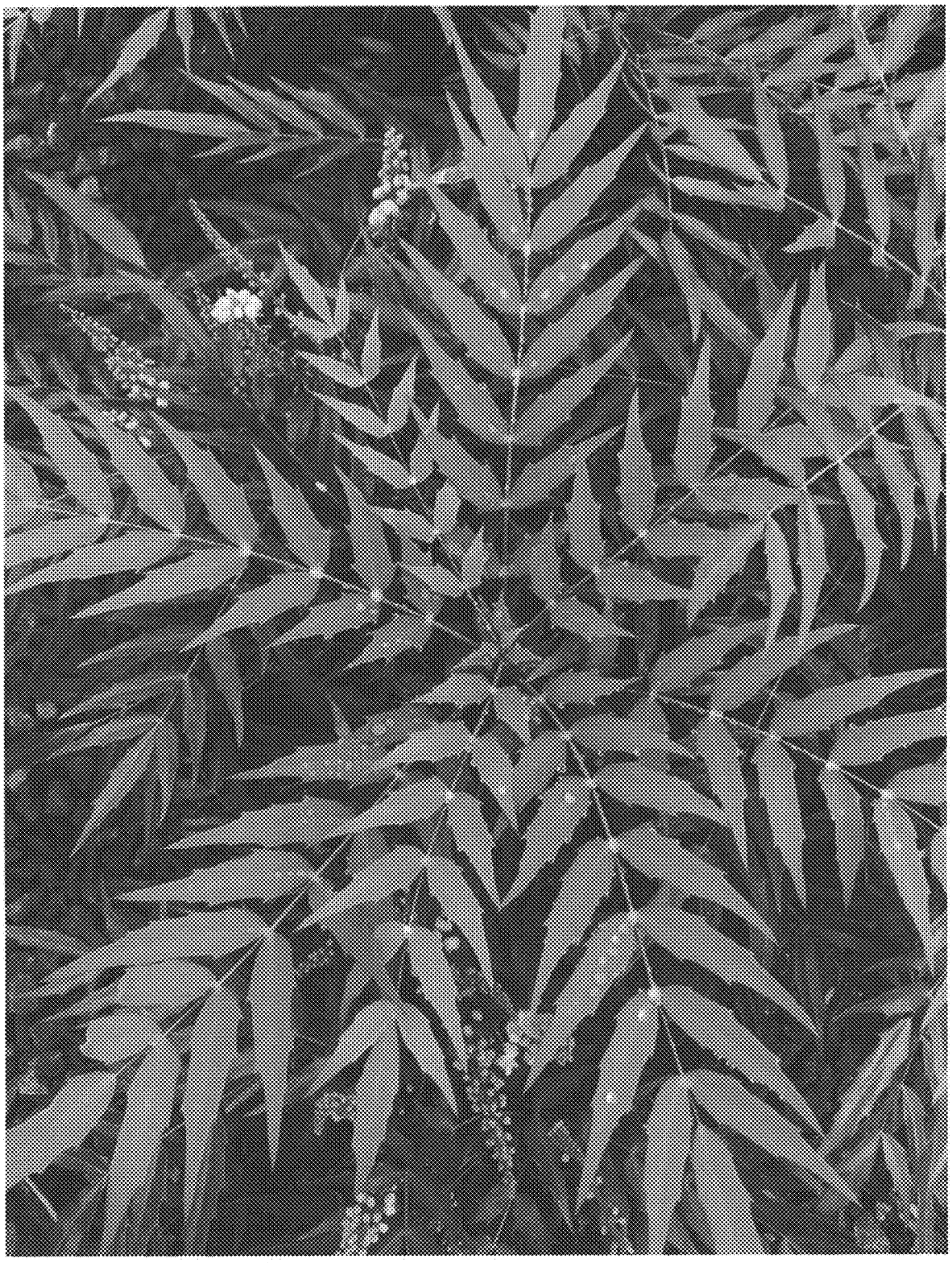
FIG. 3 is a color photograph of a typical 3-year-old specimen of *Mahonia* 'NCMH1' grown under standard horticultural practices showing the dark green (RHS 137A) lustrous foliage of 'NCMH1'.

Although *Mahonia* species are sometimes classified as *Berberis*, the most recent taxonomic treatment by Yu and Chung *Taxon* 66(6):1371-1392 (2017) classifies *Mahonia* and *Berberis* as separate genera. The following is a detailed description of the botanical characteristics of the new and distinct *Mahonia* cultivar known by the denomination 'NCMH1'. All colors cited herein refer to The Royal Horticultural Society Colour Chart designations (The Royal Horticultural Society (R.H.S.), London, Sixth Edition (2016). Where specific dimensions, sizes, colors, and other characteristics are given, it is to be understood that such characteristics are approximations or averages set forth as accurately as practicable.

The detailed descriptions reported herein were taken in 2019 from a three-year-old container-grown plant that was grown in Mills River, N.C. under standard horticultural practices. *Mahonia* 'NCMH1' has not been observed under all possible environmental conditions; therefore, the phenotype may vary under different environmental conditions such as season, temperature, light intensity, day length, cultural conditions, and the like, without however, any variance in the genotype.

TECHNICAL DESCRIPTION OF THE VARIETY

Classification:

*Botanical name.*—*Mahonia* 'NCMH1'.

*Common name.*—*Mahonia.*

*Variety name.*—'NCMH1'.

Parentage: Selected from a population of seedlings grown from a controlled cross of *Mahonia* x *media* 'Winter Sun' (unpatented) x *Mahonia* 'Soft Caress' (U.S. Plant Pat. No. 20,183).

Plant description:

*Growth habit.*—Compact and rounded shrub.

*Growth rate.*—Moderate.

*Height.*—About 100 cm.

*Width.*—About 60 cm.

Roots:

*Type.*—Fibrous.

*Root color.*—Moderate Yellow (RHS 160A).

Shoot and stem:

*Lateral branch length.*—Average is ~25 cm (~20 cm to ~30 cm).

*Lateral branch diameter.*—Average is ~0.9 cm (~0.6 cm to ~1.2 cm).

*Internode length.*—Average is ~4.5 cm (~3 cm to ~7.5 cm).

*Immature shoot texture* (*current year*).—Glabrous.

*Immature shoot color* (*current year*).—Yellow-Green (RHS N144A).

*Mature stem texture* (*from prior year*).—Glabrous with vertical fissures.

*Mature stem color* (*from prior year*).—Grey-Brown (RHS N199C).

Leaves:

*Type.*—Compound, odd-pinnate.

*Persistence.*—Evergreen.

*Leaf fragrance.*—None.

*Leaf arrangement.*—Alternate.

*Leaf length.*—Average is ~29.2 cm (~25 cm to ~37 cm).

*Leaf width.*—Average is ~10.3 cm (~7 cm to ~16 cm).

*Rachis.*—Length: Average is ~23.5 cm (~17 cm to ~26.5 cm). Width: About 0.1 cm. Color: Yellow-Green (RHS N144A). Texture: Glabrous.

*Leaflet.*—Arrangement: Opposite with terminal leaflet. Number: 13 to 19 leaflets. Shape: Lanceolate. Apex: Long acuminate. Base: Oblique to rounded. Venation: 3 to 5-nerved. Color, below: Yellow-Green (RHS 146B). Margins: Infrequently spiny-serrate with 6 to 11 teeth. Length: Average is ~7.3 cm (~3.5 cm to ~12.6 cm). Width: Average is ~1.7 cm (~0.8 cm to ~2.8 cm). Color: Emerging foliage, upper leaflet: Yellow-Green (RHS 146B). Emerging foliage, lower leaflet: Yellow-Green (RHS 146C). Mature foliage, upper leaflet: Green (RHS 137A). Mature foliage, lower leaflet: Yellow-Green (RHS 146C). Texture: Glabrous. Attachment: Sessile.

*Leaf attachment.*—Petiolate.

*Petiole.*—Length: Average is ~2 cm (~0.9 cm to ~3 cm). Diameter: About 0.2 cm. Color: Yellow-Green (RHS N144A). Texture: Glabrous.

Inflorescence:

*Description.*—Single flowers arranged on terminal racemes, opening from base to apex.

*Number of racemes per terminal.*—Average is ~9 (~5 to ~15).

*Number of flowers per raceme.*—~75 to ~100.

*Flowering season.*—November to March in Mills River, N.C.

*Fragrance.*—None.

*Lastingness.*—2 to 6 weeks.

*Raceme.*—Length: Average is ~15.8 cm (~13 cm to ~19 cm). Width: Average is ~2.2 cm (~2 cm to ~2.5 cm).

*Flower.*—Height: Average is ~0.5 cm (~0.4 cm to ~0.6 cm). Diameter: Average is ~1 cm (~0.8 cm to ~1.2 cm).

*Lastingness.*—3 to 7 days.

*Bud.*—Shape: Ovate to rounded. Length: Average is ~0.3 cm (~0.1 cm to ~0.4 cm). Diameter: Average is ~0.3 cm (~0.1 cm to ~0.4 cm). Color: Yellow (RHS 7A). Texture: Glabrous.

*Petals.*—Number: 6. Arrangement: Whorled. Length: ~0.5 cm. Width: ~0.2 cm. Shape: Oblong. Margin: Entire. Apex: Rounded. Base: Truncate. Color: Yellow (RHS 7A). Texture: Glabrous.

*Sepals.*—Number: 9, consisting of 6 petaloid sepals and 3 true sepals. Arrangement: Whorled. Petaloid sepals: Length: ~0.6 cm. Width: ~0.4 cm. Shape: Oblong. Margin: Entire. Apex: Obtuse to rounded. Base: Rounded. Color: Yellow (RHS 7A). Texture: Glabrous. True sepals: Length: About 0.3 cm. Width: Less than 0.2 cm. Shape: Oblong. Margin: Entire. Apex: Obtuse. Base: Rounded. Color: Yellow (RHS 7A) with a blush of Greyed-Red (RHS 178C). Texture: Glabrous.

*Peduncle.*—Length: Average is ~15.5 cm (~12.5 cm to ~18.5 cm). Diameter: About 0.1 cm. Color: Yellow-Green (RHS N144A). Texture: Glabrous.

*Pedicels.*—Length: Average is ~0.4 cm (~0.1 cm to ~0.6 cm). Diameter: Less than 0.1 cm. Color: Yellow-Green (RHS N144A). Texture: Glabrous.

Reproductive organs:

*Gynoecium.*—Pistil number: 1. Pistil length: ~0.4 cm. Stigma shape: Round. Stigma color: Yellow (RHS 7A). Style length: ~0.3 cm. Style color: Yellow-Green (RHS 144A).

*Androecium.*—Stamen number: 6. Stamen shape: Linear. Stamen length: About 0.4 cm. Anther shape: Two-lobed. Anther size: About 0.1 cm. Anther color: Yellow (RHS 7A). Amount of pollen: Moderate. Pollen color: Green-Yellow (RHS 1D).

Fruit and seed:

*Fruit type.*—Berry. Shape: Ovoid. Length: Average is ~1 cm (~0.8 cm to ~1.2 cm). Width: Average is ~0.4 cm (~0.3 cm to ~0.5 cm). Color: Greyed-Purple (RHS N186A). Texture: Glabrous, pruinose.

*Seed.*—None observed.

Disease and insect resistance: No significant disease or insect pests have been observed.

Cold hardiness: At least USDA zone 7b; testing has not been completed in colder zones.

COMPARISON WITH PARENTAL SPECIES

'NCMH1' is distinguished from *Mahonia* x *media* 'Winter Sun' in that 'NCMH1' has narrower evergreen leaflets, whereas *Mahonia* x *media* 'Winter Sun' has wider leaflets and fragrant flowers. 'NCMH1' is distinguished from *Mahonia* 'Soft Caress' (U.S. Plant Pat. No. 20,183) in that 'NCMH1' has wider evergreen leaflets with infrequent spines, whereas *Mahonia* 'Soft Caress' (U.S. Plant Pat. No. 20,183) has narrower leaflets with infrequent spines. 'NCMH1' also has longer racemes, up to 19 cm, whereas *Mahonia* 'Soft Caress' has racemes up to 14 cm and more flowers (about 75 to 100 per raceme) than *Mahonia* 'Soft Caress' (about 50 per raceme).

COMPARISON WITH ANOTHER *MAHONIA* CULTIVAR

'NCMH1' differs from 'NCMH2' (U.S. Plant patent application Ser. No. 17/501,735), a *Mahonia* cultivar, in that 'NCMH1' has yellow (RHS 7A) flower buds while 'NCMH2' has multicolored flower buds at the balloon stage that are vivid reddish orange (RHS 42A) with increasing amounts of vivid yellow (RHS 17C) and some strong reddish purple (RHS 72B) towards the base.

What is claimed is:

1. A new and distinct *Mahonia* plant named 'NCMH1' as illustrated and described herein.

* * * * *